United States Patent [19]

Rose et al.

[11] Patent Number: 5,277,206
[45] Date of Patent: Jan. 11, 1994

[54] PROCESS FOR PERMANENT WAVING OF HUMAN HAIR

[75] Inventors: Burkhard Rose, Darmstadt; Jürgen Tennigkeit, Seeheim, both of Fed. Rep. of Germany

[73] Assignee: Goldwell AG, Darmstadt, Fed. Rep. of Germany

[21] Appl. No.: 879,334

[22] Filed: May 7, 1992

[30] Foreign Application Priority Data

Jun. 10, 1991 [DE] Fed. Rep. of Germany ....... 4119044

[51] Int. Cl.⁵ ............................................. A45D 7/04
[52] U.S. Cl. ................................. 132/204; 424/71; 424/72
[58] Field of Search .............. 132/202, 203, 204, 205; 424/70, 71, 72

[56] References Cited

U.S. PATENT DOCUMENTS

| | | | |
|---|---|---|---|
| 3,583,408 | 6/1971 | Wall | 132/204 |
| 3,633,591 | 1/1972 | Anzuino et al. | 132/204 |
| 3,676,546 | 7/1972 | Ghilardi et al. | 424/71 |
| 3,736,944 | 6/1973 | Ghilardi et al. | 132/204 |
| 4,366,827 | 1/1983 | Madrange et al. | 132/204 |
| 4,608,250 | 8/1986 | Jacquet et al. | 132/204 |
| 4,659,566 | 4/1987 | Petrow | 132/204 |
| 4,848,377 | 7/1989 | Bires et al. | 132/207 |
| 4,992,586 | 2/1991 | Junino et al. | 564/367 |

*Primary Examiner*—Gene Mancene
*Assistant Examiner*—Frank A. LaViola
*Attorney, Agent, or Firm*—Birch, Stewart, Kolasch & Birch

[57] ABSTRACT

A mild permanent waving process for human hair including the steps of applying a reducing composition containing at least one thio compound, subsequently pre-fixing with a composition containing at least one dithio compound without previous rinsing, and finally fixing with a composition containing an oxidant, especially hydrogen peroxide, in a low concentration.

8 Claims, No Drawings

PROCESS FOR PERMANENT WAVING OF HUMAN HAIR

The present invention concerns a process for permanent waving of human hair improving the characteristics of permed hair thereby.

It is known that a permanent wave requires two steps for treatment: a reductive splitting cystine of disulfide bridges by action of a reducing agent. A subsequent the fixing by the use of an oxidant reproducing these cystine disulfide bridges.

As emerges from the German pioneer patents Nos. 948 186 and 972 424, the classical reducing agent is thioglycolic acid, e.g. as an ammonium or monoethanolamine salt, which has been partially replaced by glycerol monothioglycollate in the past few years; on the other hand, thiolactic acid and its esters, as well as inorganic sulfites are also applied for this purpose.

The compositions containing thioglycolic acid have a pH-value of around 7.5 to 9.0, especially 8.5 to 9.0, whereas the alkalization normally will be effected by adding ammonium (bi)carbonate and/or ammonia. The repeated application of strong alkaline reducing agents and subsequent fixing with an oxidant may cause further damage to the hair, especially regarding which is not totally intact hair which has been, e.g. pre-damaged due to bleaching or alkaline oxidation dyeing. The same applies for the fixing using a high concentration of oxidants of about 2–4% by weight, based on hydrogen peroxide.

The present invention is a process for the permanent waving of human hair leading to a mild but effective waving in connection with keeping resilience and elasticity of permed hair. This problem is resolved by applying a reducing agent composition containing at least one thio compound in the usual way to the hair. Subsequently, without prior rinsing, a pre-fixation is carried out by treatment with a composition containing at least one compound having a dithio group. The treated hair is then rinsed and finally fixed in the usual way with an oxidant composition wherein the concentration of the oxidant based on hydrogen peroxide is only about 0.5 to 1.5% by weight of the total fixing composition. Compared with the conventional treatment, this new process keeps the hair substantially more elastic.

It is believed that the pre-fixing step with dithio compounds already re-establishes a major part of the disulfide groups in the hair.

German Offenlegungsschrift No. 37 07 415 discloses a process for permanent waving by applying a mixture of separately kept two-component preparations wherein one component contains a thioglycolic acid ester, and the other contains an aqueous solution of dithio diglycolic acid, dithiolactic acid or their salts in aqueous solution together with alkali or ammonium carbonate. The multiple step process of the present invention is in no way suggested by this reference.

German Offenlegungsschrift No.22 63 203 describes a process for perming human hair by treating hair in a first step with a shaping agent based on thioglycolic acid or thiolactic acid and their salts and in a second step with another part of the waving agent containing additional hydrophilic thioglycolic acid or thiolactic acid ester. The advantageous effects of the process according to the present invention ar not achieved by this known method.

The reducing agents are used as aqueous solutions, gels, emulsions (creams) or also as aerosol foams and may contain, besides reducing and alkalizing substances, conditioning compounds such as cationic polymers, optionally thickening substances, so-called carriers which especially increase the penetration of the product, complexing agents, opacifiers, fragrances and, for improving wetting and penetration ability, also surface-active substances.

Major ingredients for the fixing resp. neutralizing agents are oxidants. The most frequent oxidant is hydrogen peroxide with a concentration of 0.5 to 1.5% by weight according to the invention, which is significantly below the common concentration used hitherto. Other useful oxidants are alkali bromates, urea peroxide and sodium perborate; the last two are used in water-free products.

These compositions are preferably used as aqueous solutions or as aerosol foams, less often as gels. They may contain different additives, e.g. stabilizers, plant extracts, hair conditioning substances, and surfactants.

As already mentioned, the following reducing agents may be used in permanent waving methods according to the invention:

Besides inorganic sulfites such as sodium bisulfate, especially thioglycolic acid and ammonium thioglycolate, thiolactic acid, its salts and esters, 2-mercaptoethylamine, cysteine and its hydrochloride, cysteamine, N-acetylcysteine, thioacetic acid, its salts and esters as well as especially thioglycolic acid monoglycerol ester are suitable reducing agents. In case of its application or the application of similar thioesters, the mixing with the residual aqueous part of the reducing agent compositions occurs immediately prior to application onto the hair.

The usage concentration of the reducing substance depends on its structure and usually is between approximately 2.5 and 15% by weight of the reducing composition, preferably between approximately and 10% by weight.

The amount of alkalizing agent depends on the reducing agent. The composition contains preferably 1 to 10% by weight, optimally 2 to 8% by weight. A preferred alkalizing agent within the scope of the invention is ammonium carbamate used by itself or in combination with further alkalizing agents such as ammonia and/or ammonium (bi)carbonate. The pH-value is ideally adjusted between approximately 7 and 9. The permanent waving compositions applied according to the invention preferably also contain surfactants. Their percentage is around 0.2 to approximately 10, preferably 1 to 5% by weight.

In both the reducing agent and the fixing composition, it is preferred to use anionic surfactants, optionally in combination with non-ionic surfactants.

Suitable anionic surfactants are especially the well-known alkyl ether sulfates and carboxylic acids, particularly as alkali salts, as well as protein fatty acid condensates.

Suitable non-ionic surfactants are especially $C_8$–$C_{18}$-fatty alcohol polyglycolethers, fatty acid polyglycolesters, fatty acid alkanolamides, amine oxides, and first of all, $C_8$–$C_{18}$-alkyl polyglycosides. Amphoteric surfactants like betaines and sulfo-betaines as well as, especially in cationic fixings, cationic surfactants may be used, e.g. quaternary ammonium salts.

Additional ingredients of the reducing composition according to the invention are $C_3$–$C_6$-alkanediols and their ethers, especially the mono-$C_1$–$C_3$-alkylethers. Preferred substances in this respect are 1,2- and 1,3-propanediol, 1-methoxy-propanol(-2), 1-ethoxy-propanol(-2), 1,3- and 1,4-butanediol, diethyleneglycol and its monomethyl and monoethyl ether as well as dipropyleneglycol and its monomethyl and monoethyl ether. The percentage of these diols is preferably between 1 and 30, preferably approximately 2.5 to 15, ideally approximately 5 to 10% by weight of the total reducing composition.

Besides the $C_3$–$C_6$-alkanediols and their ethers, also propylenecarbonate (4-methyl-1,3-dioxolane 2-one), N-alkyl pyrrolidones, glycerol and urea may be used.

The compositions applied according to the invention of course may contain all substances generally used in hair waving compositions, which are not listed here in detail.

To avoid repetition, attention is drawn to the prior art as stated e.g. in "Ullmann's Encyclopedia of Industrial Chemistry", Vol. A12 (1986), pp. 588 to 591, and especially in the monography of K. Schrader, "Grundlagen und Rezepturen der Kosmetika", 2nd Ed. (1989, Hüthig Buch Verlag), pp. 823 to 840, as well as the general review article of D. Hollenberg et al in "Seifen-Öle-Fette-Wachse", Vol.117 (1991), pp.81–87, which are incorporated herein by reference.

The compositions used for the "pre-fixings" according to the invention include dithio groups, preferably dithio diglycolic acid, dithio dilactic acid as well as their esters and alkali and ammonium salts, preferably in amounts between 2.5 and approximately 10, preferably approximatley 4 to 7% by weight of the composition. An additional dithio group bearing substance may be cysteine. If required, prior to applying the reducing agent a pre-treatment may be carried out as described e.g. in German Offenlegungsschrift No.37 40 926. After application of this pre-treatment, the hair is rolled up and the reducing agent is applied. After 15 to 20 minutes effecting time, the pre-fixing agent containing at least one dithio group is applied without previous rinsing for about 3 to 8, preferably about 5 minutes.

The process according to the invention offers the additional possibility of dosing the pre- or intermediate treatment differently on the single hair strands depending on the necessity. Subsequently, it is rinsed and fixed as usual with the fixing agent based on an oxidation substance such as hydrogen peroxide in low concentration.

The following examples illustrate the invention.

EXAMPLE 1

A solution of the following composition is applied to hair which has been treated with a conventional and commercial mild-alkaline perm:

| | |
|---|---|
| Dithio diglycolic acid, diammonium salt (40%) | 12.50% by wt. |
| Glycerol | 5.00 |
| Ammonium bicarbonate | 0.50 |
| Lauryl polyglycolether | 0.50 |
| Fragrance | 0.20 |
| Demineralized water ad | 100.00 |

After 5 minutes the hair is rinsed thoroughly and subsequently "fixed" with the following oxidant composition:

| | |
|---|---|
| Hydrogen peroxide | 1.00% by wt. |
| Sodium lauryl diglycolether sulfate | 5.00 |
| Phenacetin | 0.02 |
| Phosphoric acid for adjustment to pH 3.5 | q.s. |
| Demineralized water ad | 100.00 |

A shiny, well-permed hair is obtained with measurably improved elasticity and resilience in comparison to conventionally permed hair.

EXAMPLE 2

The following composition is applied to hair which has been treated with a mild-acidic perm liquid on the base of glycerol monothioglycolic acid ester:

| | |
|---|---|
| Diammonium dithio diglycollate (40%) | 8.75% by wt. |
| 1,2-Propanediol | 5.00 |
| Disodium hydrogenphosphate | 0.50 |
| PEG-40-hydrogenated castor oil | 0.50 |
| Protein hyrolyzate | 1.00 |
| Fragrance | 0.20 |
| Water ad | 100.00 |

After approximatley 4 minutes the hair is rinsed well with water and subsequently "fixed" with the following composition in the usual way:

| | |
|---|---|
| Hydrogen peroxide | 1.20% by wt. |
| Cationic polymer (Polyquaternium-10) | 0.25 |
| Cocosamine oxide | 1.00 |
| Phenacetin | 0.02 |
| Nonylphenol polyglycolether | 0.50 |
| Fragrance | 0.10 |
| Phosphoric acid for pH-adjustment to 2.8 | q.s. |
| Demineralized water ad | 100.00 |

A well-permed hair with good resilience and elasticity is obtained.

EXAMPLE 3

The following composition is suitable for a pre-fixing in the sense of the invention in combination with the usual perm liquids:

| | |
|---|---|
| Diammonium dithio diglycollate (40%) | 4.50% by wt. |
| Ethyl carbitol | 7.50 |
| Ammonium bicarbonate | 1.00 |
| Nonylphenol polyglycolether | 1.00 |
| Cationic polymer (Polyquaternium-10) | 0.10 |
| Fragrance | 0.30 |
| Demineralized water ad | 100.00 |

"End-fixing" can be effected with the following solution:

| | |
|---|---|
| Hydrogen peroxide | 0.90% by wt. |
| Phenacetin | 0.02 |
| Fragrance | 0.10 |
| Sodium lauryl sulfate | 2.50 |
| Phosphoric acid for pH-adjustment to 3.5 | q.s |
| Demineralized water ad | 100.00 |

The following formula is a characteristic one for a suitable reducing agent composition according to the invention:

| | |
|---|---|
| Thioglycolic acid (80%) | 10.00% by wt. |
| Ammonium carbamate | 6.00 |
| Ammonia | 1.10 |
| Cocosamido propylbetaine | 2.00 |
| 1,2-Propanediol | 5.00 |
| Fragrance | q.s. |
| Water ad | 100.00 |

We claim:

1. A process for the permanent waving of human hair, comprising the following steps:
   a) applying to the hair a reducing agent composition comprising at least one thio compound and at least one alkalizing agent;
   b) subsequently pre-fixing by applying a composition containing at least one dithio compound;
   c) finally fixing by treating with an oxidizing composition, wherein the concentration of the oxidant is between 0.5 and 1.5% by weight, calculated on hydrogen peroxide based on the total weight of said oxidizing composition.

2. The process according to claim 1, wherein said reducing agent composition comprises 2.5 to 15% by weight, calculated on the total composition, of a thio compound selected from the group consisting of thioglycolic acid, thioacetic acid, thiolactic acid and ammonium salts thereof; thioglycolic acid glycerol ester; thiolactic acid glycerol ester; cysteine; N-acetylcysteine; cysteamine; 2-mercaptoethylamine; inorganic sulfites; and mixtures thereof.

3. The process according to claim 2, wherein said thio compound is selected from the group consisting of sodium bisulfate and ammonium bisulfite.

4. The process according to claim 1, wherein at least part of said alkalizing agents comprises ammonium carbamate.

5. The process according to claim 1, wherein said pre-fixing composition constant about 2.5 to about 10% by weight of dithio diglycolic acid, dithio dilactic acid, and esters, alkali and ammonium salts thereof as said dithio compounds.

6. The process according to claim 5, wherein said pre-fixing composition comprises about 4 to about 7% by weight of said dithio compound, calculated on the total composition thereof.

7. The process according to claim 1, wherein step b) follows step a) without an intermediate rinsing step.

8. The process according to claim 1, further comprising a rinsing step following said pre-fixing step b) and prior to said final fixing step c).

* * * * *